US012811010B2

(12) United States Patent
Tanaka et al.

(10) Patent No.: US 12,811,010 B2
(45) Date of Patent: *Nov. 24, 2026

(54) DEPRESSIVE SYMPTOM DETERMINATION APPARATUS, DETERMINATION MODEL GENERATION APPARATUS, AND METHOD OF GENERATING TRAINING DATA

(71) Applicants: FRONTEO, Inc., Tokyo (JP); Keio University, Tokyo (JP)

(72) Inventors: Yuichiro Tanaka, Tokyo (JP); Hiroyoshi Toyoshiba, Tokyo (JP); Masato Homma, Tokyo (JP); Takashi Matsumoto, Tokyo (JP); Taishiro Kishimoto, Tokyo (JP)

(73) Assignees: FRONTEO, Inc., Tokyo (JP); KEIO UNIVERSITY, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 19/121,215

(22) PCT Filed: Jul. 12, 2023

(86) PCT No.: PCT/JP2023/025679
§ 371 (c)(1),
(2) Date: Apr. 15, 2025

(87) PCT Pub. No.: WO2025/013234
PCT Pub. Date: Jan. 16, 2025

(65) Prior Publication Data

US 2026/0142031 A1 May 21, 2026

(51) Int. Cl.
*G16H 50/20* (2018.01)

(52) U.S. Cl.
CPC .................................. *G16H 50/20* (2018.01)

(58) Field of Classification Search
CPC ...................................................... G16H 50/20
See application file for complete search history.

(56) References Cited

U.S. PATENT DOCUMENTS 10,812,424 B1 10/2020 Bommaraju
11,633,103 B1 4/2023 Nudd
(Continued)

FOREIGN PATENT DOCUMENTS

CN 111241817 A * 6/2020 ............. G16H 50/20
WO 2006100675 A2 9/2006
(Continued)

OTHER PUBLICATIONS

Higuchi M et al.; Detection of Major Depressive Disorder Based on a Combination of Voice Features: An Exploratory Approach. Int J Environ Res Public Health. Sep. 10, 2022;19(18):11397 (Year: 2022).*

(Continued)

*Primary Examiner* — Joshua B Blanchette
(74) *Attorney, Agent, or Firm* — POLSINELLI PC

(57) ABSTRACT

A depressive symptom determination unit 13 configured to determine a depressive symptom of a subject by inputting a feature vector generated based on a feature quantity of a conversation conducted by a determination target subject to a machine-trained determination model is provided, and determination is performed by a determination model generated by machine learning using, as training data, conversation data of a subject satisfying a predetermined extraction condition and exclusion condition with regard to the depressive symptom. By labeling training data with a positive example/negative example based on a HAMD score while an extraction condition is set based on a diagnosis result of a doctor, a depressive symptom can be determined according to a state of a subject when a conversation is conducted even for a subject temporarily in a state different from a diagnosis result for a depressive symptom by a doctor.

6 Claims, 4 Drawing Sheets

(56) References Cited

U.S. PATENT DOCUMENTS

| | | | | |
|---|---|---|---|---|
| 2012/0208712 | A1 | 8/2012 | Sibille | |
| 2015/0318002 | A1* | 11/2015 | Karam | A61B 5/4803 704/231 |
| 2015/0370993 | A1 | 12/2015 | Moturu | |
| 2021/0233660 | A1* | 7/2021 | Omiya | G10L 25/66 |
| 2022/0059226 | A1* | 2/2022 | Kishimoto | G16H 50/70 |

FOREIGN PATENT DOCUMENTS

| | | | |
|---|---|---|---|
| WO | 2020/013302 | A1 | 1/2020 |
| WO | 2020/122227 | A1 | 6/2020 |

OTHER PUBLICATIONS

Perlis, Roy; "Clinical Features of Bipolar Depression Versus Major Depressive Disorder in Large Multicenter Trials." American Journal of Psychiatry, vol. 163, No. 2 (Year: 2006).*

Mitchell PB, Frankland A, Hadzi-Pavlovic D, et al. Comparison of depressive episodes in bipolar disorder and in major depressive disorder within bipolar disorder pedigrees. Br J Psychiatry. 2011;199(4):303-309. doi: 10.1192/bjp.bp. 110.088823 (Year: 2011).*

Takano T, Mizuguchi D, Omiya Y, et al. Estimating Depressive Symptom Class from Voice. Int J Environ Res Public Health. 2023; 20(5):3965. Published Feb. 23, 2023. doi: 10.3390/ijerph20053965 (Year: 2023).*

Yamamoto et al., "Using speech recognition technology to investigate the association between timing-related speech features and depression severity," Plos One | https://doi.org/10.1371/journal.pone.0238726 Sep. 11, 2020 (Year: 2020).*

Yamamoto et al., "Using speech recognition technology to investigate the association between timing-related speech features and depression severity" https://doi.org/10.1371/journal.pone.0238726 (Year: 2020).*

Quoc Le and Tomas Mikolov, "Distributed Representations of Sentences and Documents" arXiv:1405.4053 (Year: 2014).*

International Search Report and Written Opinion issued on Sep. 26, 2023 for corresponding PCT Application No. PCT/JP2023/025679.

Kim, Ah Young et al., Automatic Depression Detection Using Smartphone-Based Text-Dependent Speech Signals: Deep Convolution Neural Network Approach, Journal of Medical Internet Research, Jan. 25, 2023, vol. 25, p. e34474, D01: 10.2196/34474.

Non-Final Office Action mailed on Apr. 30, 2026 in related U.S. Appl. No. 19/121,154.

International Search Report and Written Opinion issued on Sep. 26, 2023 for PCT Application No. PCT/JP2023/025678 counterpart of U.S. Appl. No. 19/121,154.

Ito, Masumi: "Neuropsychiatric evaluations ofpostictal behavior changes", Epilepsy & Behavior, vol. 19, 2010, pp. 134-137.

Extended European Search Report issued on Apr. 23, 2026 for European Application No. 23943949.0 counterpart of U.S. Appl. No. 19/121,154.

Khorram, S. et al.: "Recognition of Depression in Bipolar Disorder: Leveraging Cohort and Person-Specific Knowledge", Interspeech, Sep. 8-12, 2016, pp. 1215-1219 XP093108756.

Faurholt-Jepsen, M. et al.: "Voice analysis as an objective state marker in bipolar disorder", Translational Psychiatry.vol. 6, No. 7, 2016, pp. e856-e856 XP055445381.

Extended European Search Report issued on Apr. 22, 2026 for counterpart European Application No. 23943955.7.

Shin, Daun et al.: "Detection of Minor and Major Depression through Voice as a Biomarker Using Machine Learning", Journal of Clinical Medicine, vol. 10, No. 14, Jul. 8, 2021, pp. 1-15 XP093343111.

Dubovsky, Steven L. et al.: "Bipolar Disorder: Comprehensive Update", Feb. 3, 2020, pp. 1-89 XP093343115.

Mullen, Michael T. et al.: "Internet-based Cognitive Behavioral Therapy to Reduce Depressive Symptoms after Stroke Pilot/ Feasibility Study", Dec. 13, 2018, pp. 1-32 XP093343131.

* cited by examiner

Fig. 5

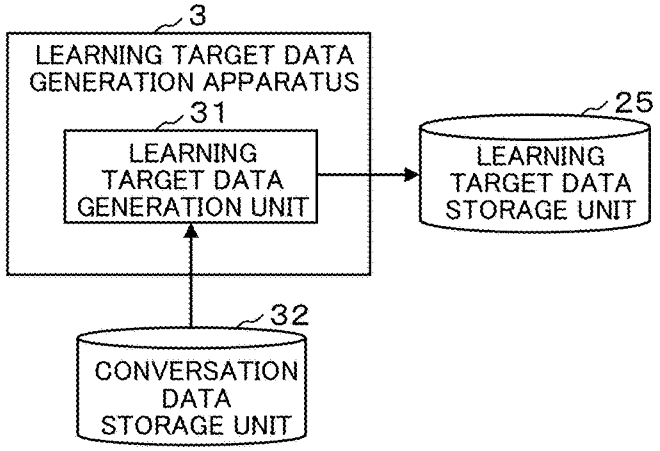

Fig. 6

| GROUND TRUTH (HAMD SCORE) | DETERMINATION RESULT BY DEPRESSIVE SYMPTOM DETERMINATION APPARATUS | |
|---|---|---|
| | HAMD SCORE IS LESS THAN 8 POINTS | HAMD SCORE IS 8 POINTS OR MORE |
| HAMD SCORE IS LESS THAN 8 POINTS | TRUE NEGATIVE (TN) : 12 | FALSE POSITIVE (FP) : 8 |
| HAMD SCORE IS 8 POINTS OR MORE | FALSE NEGATIVE (FN) : 4 | TRUE POSITIVE (TP) : 47 |

Fig. 7

| GROUND TRUTH (HAMD SCORE) | DETERMINATION RESULT BY DEPRESSIVE SYMPTOM DETERMINATION APPARATUS | |
|---|---|---|
| | HAMD SCORE IS LESS THAN 8 POINTS | HAMD SCORE IS 8 POINTS OR MORE |
| HAMD SCORE IS LESS THAN 8 POINTS | TRUE NEGATIVE (TN) : 0 | FALSE POSITIVE (FP) : 0 |
| HAMD SCORE IS 8 POINTS OR MORE | FALSE NEGATIVE (FN) : 18 | TRUE POSITIVE (TP) : 73 |

Fig. 8
(a)
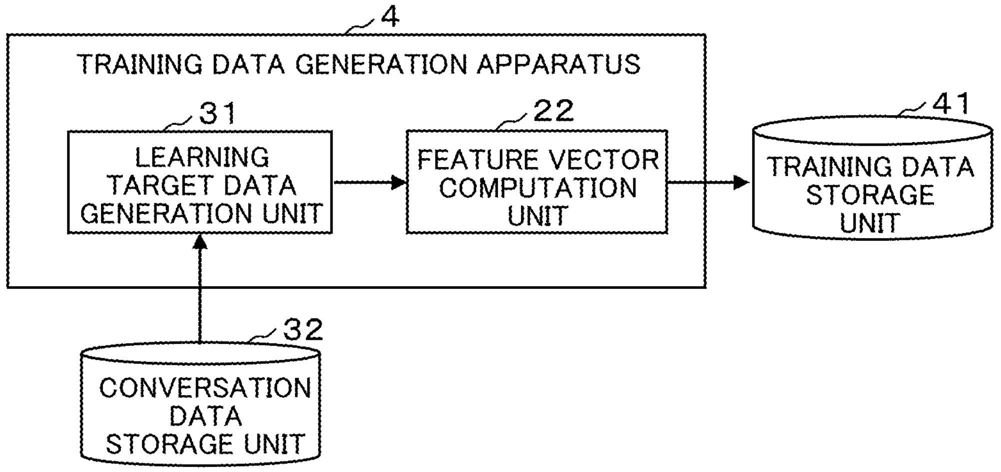
(b)
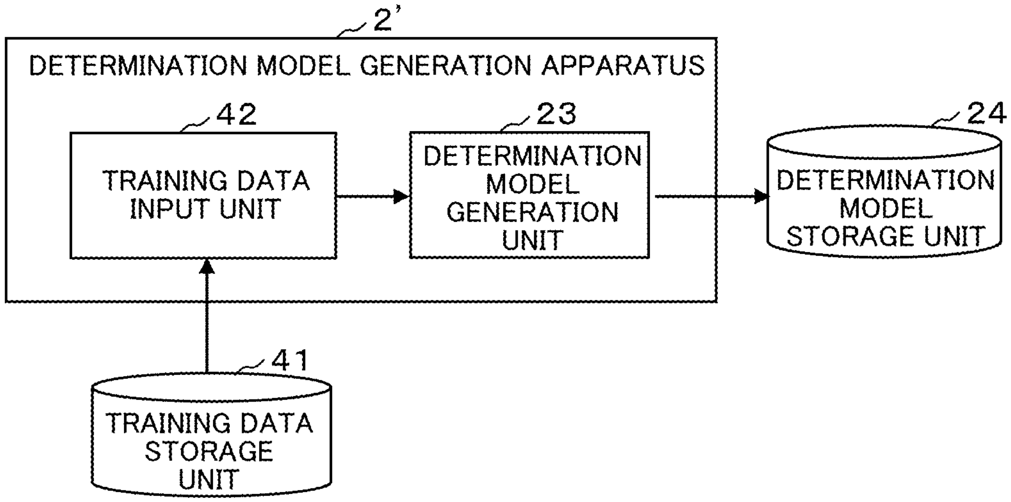

DEPRESSIVE SYMPTOM DETERMINATION APPARATUS, DETERMINATION MODEL GENERATION APPARATUS, AND METHOD OF GENERATING TRAINING DATA

CROSS REFERENCE TO RELATED APPLICATIONS

This application is a National Phase filing under 35 U.S.C. § 371 of PCT/JP/2023/025679, filed on Jul. 12, 2023; the entire contents of which application is hereby incorporated by reference.

TECHNICAL FIELD

The present invention relates to a depressive symptom determination apparatus, a determination model generation apparatus, and a method of generating training data, and particularly relates to an apparatus for determining a depressive symptom of a person using a machine-trained determination model, an apparatus for generating the determination model, and a method of generating training data used in machine learning.

BACKGROUND ART

Conventionally, there has been a known technology for estimating presence/absence or severity of a depressive state by an estimation model trained using teacher data (for example, see Patent Literature 1: WO2020/122227). This Patent Literature 1 discloses that an estimation model is trained by machine learning in which a plurality of types of feature quantities extracted from biometric data of each subject is used as input vectors, and using teacher data in which evaluation of presence/absence of a depressive state by an expert such as a doctor for each subject is used as a label.

In addition, Patent Literature 1 shows that the Hamilton Depression Scale (HAMD), which is a common diagnostic index for depression, is used to diagnose depression by a doctor, and that a cutoff value for an evaluation value based on HAMD-17 is set at 7 points, and when a total score exceeds 7 points, it is determined that depression has developed. In HAMD-17, an expert such as a doctor asks questions for 17 items to evaluate a degree based on answers obtained from a subject, and a diagnosis is performed so that the degree is normal when a total value of a score (hereinafter referred to as HAMD score) of 3 to 5 points for each item is 0 to 7 points, the degree is mild when the total value is 8 to 13 points, the degree is moderate when the total value is 14 to 18 points, the degree is severe when the total value is 19 to 22 points, and the degree is extremely severe when the total value is 23 points or more.

SUMMARY OF INVENTION

Technical Problem

In the technology described in Patent Literature 1, by configuring an estimation model to estimate the HAMD score, it is possible to distinguish between a healthy person whose estimation value of the HAMD score is 7 points or less and a depressed patient whose estimation value is 8 points or more, or to estimate severity of a depressed patient. However, the technology described in Patent Literature 1 does not take into account that the HAMD score may vary depending on the psychological state of the subject at the time, and has a problem in that it is impossible to determine a depressive symptom of the subject at the time.

The invention has been made to solve such a problem, and an object of the invention is to make it possible to determine the depressive symptom of the subject at the time using a machine-trained determination model.

Solution to Problem

To solve the above-mentioned problem, in the invention, a depressive symptom of a subject is determined by inputting a feature vector computed based on a feature quantity of a conversation conducted by a determination target subject to a machine-trained determination model. The determination model is machine-trained using, as training data, a feature vector of a plurality of subjects satisfying a predetermined extraction condition and exclusion condition with regard to the depressive symptom. Here, the extraction condition is a condition for extracting a subject diagnosed with depression and a subject not diagnosed with either manic-depressive or depression, and the exclusion condition is a condition for excluding a subject whose predetermined manic-depressive evaluation scale score is greater than or equal to a manic-depressive threshold. In addition, the training data is configured using, as a positive example, a subject whose depression evaluation scale score is greater than or equal to a depression threshold and using, as a negative example, a subject whose depression evaluation scale score is less than the depression threshold among subjects satisfying an extraction condition and an exclusion condition.

Advantageous Effects of Invention

According to the invention configured as described above, a depressive symptom is determined based on a feature of a conversation conducted by a determination target subject using a determination model machine-trained using a feature vector computed based on a feature quantity of a conversation, and thus it is possible to determine a depressive symptom when a subject is conducting a conversation. In addition, while an extraction condition is set based on a diagnosis result of a doctor, training data is labeled with a positive example/negative example based on a HAMD score. Therefore, a depressive symptom can be determined according to a state of a subject when a conversation is conducted even for a subject temporarily in a state different from a diagnosis result for a depressive symptom by a doctor. In this way, a depressive symptom of the subject at the time can be determined by a determination model regardless of the diagnosis result for the depressive symptom by the doctor.

In addition, according to the invention, a depressive symptom of a determination target subject can be determined with high accuracy by a determination model machine-trained without being affected by a feature vector of a subject whose depression evaluation scale score becomes less than the depression threshold when the manic-depressive disorder is temporarily in a manic state.

BRIEF DESCRIPTION OF DRAWINGS

FIG. 5 is a block diagram illustrating a functional configuration example of a learning target data generation apparatus according to this embodiment.

FIG. 6 is a diagram illustrating a result of determining a depressive symptom using the depressive symptom determination apparatus of this embodiment.

FIG. 7 is a diagram illustrating a result of determining a depressive symptom using the depressive symptom determination apparatus of this embodiment.

FIG. 8 is block diagrams illustrating functional configuration examples of a training data generation apparatus and the determination model generation apparatus according to this embodiment.

DESCRIPTION OF EMBODIMENTS

Figure 1:
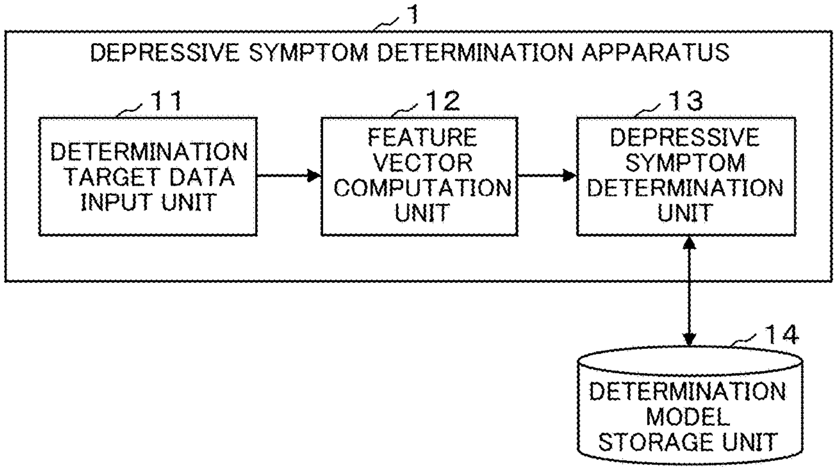
FIG. 1 is a block diagram illustrating a functional configuration example of a depressive symptom determination apparatus according to this embodiment.

Hereinafter, an embodiment of the invention will be described with reference to the drawings. FIG. 1 is a block diagram illustrating a functional configuration example of a depressive symptom determination apparatus 1 according to this embodiment. As illustrated in FIG. 1, the depressive symptom determination apparatus 1 of this embodiment includes, as a functional configuration, a determination target data input unit 11, a feature vector computation unit 12, and a depressive symptom determination unit 13. In addition, a determination model storage unit 14 is connected to the depressive symptom determination apparatus 1 of this embodiment as a storage medium.

The functional blocks 11 to 13 can be configured by any of hardware, a DSP (Digital Signal Processor), and software. For example, the functional blocks 11 to 13 are realized by an operation of a program stored in a storage medium such as a RAM, a ROM, a hard disk, or a semiconductor memory under the control of a microcomputer including a CPU, a RAM, a ROM, etc. Instead of or in addition to the CPU, a GPU (Graphics Processing Unit), an FPGA (Field Programmable Gate Array), an ASIC (Application Specific Integrated Circuit), a DSP, etc. may be used.

The determination target data input unit 11 inputs, as determination target data, m pieces of conversation data each representing content of a conversation that m subjects (m being any integer greater than or equal to 1) who are determination targets of a depressive symptom conducts. In this embodiment, as an example of conversation data, character data of a text representing content of the conversation is input as the determination target data.

For example, the determination target data input unit 11 replaces voice data of a series of conversations between a doctor and a subject whose depressive symptom is unknown with character data, extracts character data of a speech part of the subject from the data, and inputs the character data as determination target data.

The conversations between the subject and the doctor take place as a medical interview, and last, for example, 5 to 10 minutes. In other words, a conversation in which the doctor asks the subject a question and the subject answers the question is repeatedly performed. The conversation at this time is recorded using a microphone, and voice data of the conversation is converted into character data by manual transcription or using automatic voice recognition technology.

Here, when a plurality of exchanges is made between the subject and the doctor, a plurality of speech parts by the subject and the doctor is included in the series of conversations. In this embodiment, as an example, character data of the plurality of speech parts is collectively treated as one text. That is, for one conversation (series of dialogue) of one subject, in general, a text including two or more sentences separated by periods is defined as one text. This means that, when the determination target data input unit 11 inputs determination target data of m subjects, m texts are input.

The feature vector computation unit 12 computes a feature quantity of conversation data input by the determination target data input unit 11 and converts the feature quantity into a vector, thereby obtaining a feature vector. When text (character data) representing content of a conversation is used as an example of conversation data, the feature vector computation unit 12 computes a feature quantity of the text and converts the feature quantity into a vector. Calculation content for conversion into a vector is any calculation content. However, for example, the feature vector can be computed using a method illustrated in FIG. 2.

Figure 2:
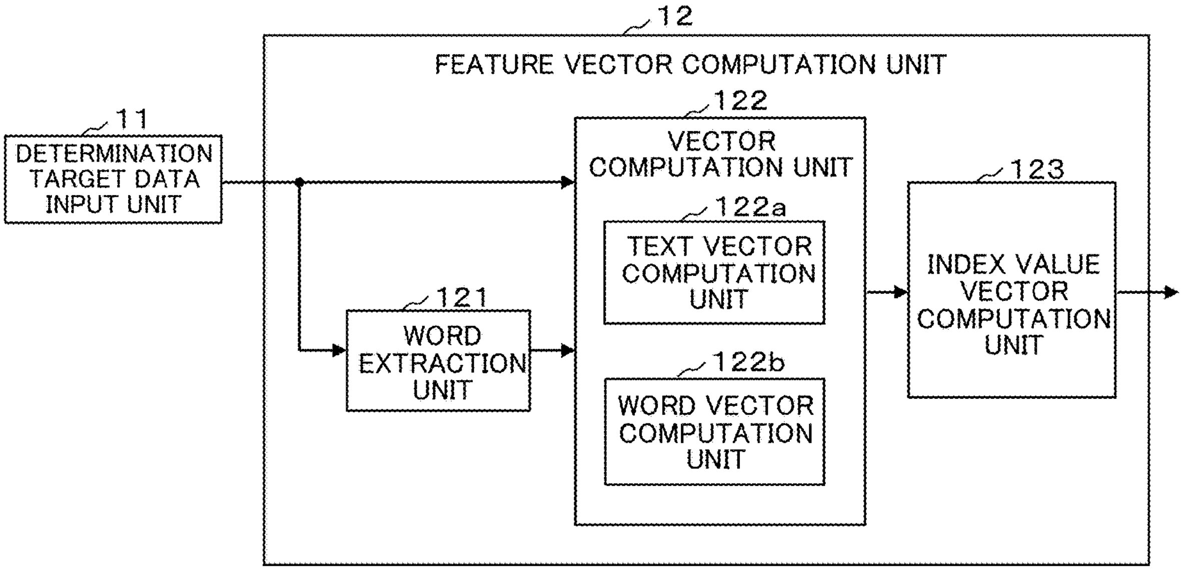
FIG. 2 is a block diagram illustrating a specific functional configuration example of a feature vector computation unit according to this embodiment.

FIG. 2 is a block diagram illustrating a specific functional configuration example of the feature vector computation unit 12. As illustrated in FIG. 2, the feature vector computation unit 12 includes a word extraction unit 121, a vector computation unit 122 and an index value vector computation unit 123 as functional configurations. The vector computation unit 122 includes a text vector computation unit 122*a* and a word vector computation unit 122*b* as more specific functional configurations.

The word extraction unit 121 analyzes m texts input as determination target data by the determination target data input unit 11 and extracts n words (n is an arbitrary integer of 2 or more) from the m texts. As a method of analyzing texts, for example, a known morphological analysis can be used. The word extraction unit 121 may extract morphemes of all parts of speech divided by the morphological analysis as words, or may extract only morphemes of a specific part of speech as words.

Note that the same word may be included in the m texts a plurality of times. In this case, the word extraction unit 121 does not extract the plurality of the same words, and extracts only one. That is, the n words extracted by the word extraction unit 121 refer to n types of words. Here, the word extraction unit 121 may measure a frequency at which the same word is extracted from m texts, and extract n (n types of) words in descending order of occurrence frequencies, or n (n types of) words each having an occurrence frequency greater than or equal to a threshold.

The vector computation unit 122 computes m text vectors and n word vectors from the m texts and the n words. Here, the text vector computation unit 122*a* converts each of the m texts to be analyzed by the word extraction unit 121 into a q-dimensional vector (q is an arbitrary integer of 2 or more) according to a predetermined rule, thereby computing the m text vectors including q axis components. In addition, the word vector computation unit 122*b* converts each of the n words extracted by the word extraction unit 121 into a q-dimensional vector according to a predetermined rule, thereby computing the n word vectors including q axis components.

In the present embodiment, as an example, a text vector and a word vector are computed as follows. Now, a set $S=\langle d \in D, w \in W \rangle$ including the m texts and the n words is considered. Here, a text vector $d_i$→ and a word vector $w_j$→ (hereinafter, the symbol "→" indicates a vector) are associated with each text $d_i$ (i=1, 2, . . . , m) and each word $w_j$ (j=1, 2, . . . , n), respectively. Then, a probability $P(w_j|d_i)$ shown in the following Equation (1) is calculated with respect to an arbitrary word $w_j$ and an arbitrary text $d_i$.

[Equation 1]

$$P(w_j \mid d_i) = \frac{\exp\left(\vec{w}_j \cdot \vec{d}_i\right)}{\sum_{k=1}^{n} \exp\left(\vec{w}_j \cdot \vec{d}_i\right)} \tag{1}$$

Note that the probability $P(w_j|d_i)$ is a value that can be computed in accordance with a probability p disclosed in, a thesis "'Distributed Representations of Sentences and Documents' by Quoc Le and Tomas Mikolov, Google Inc; Proceedings of the 31st International Conference on Machine Learning Held in Bejing, China on 22-24 Jun. 2014" describing evaluation of a text or a document using a paragraph vector. This thesis states that, for example, when there are three words "the", "cat", and "sat", "on" is predicted as a fourth word, and a computation formula of the prediction probability p is described. The probability p(wt|wt−k, . . . , wt+k) described in the thesis is a correct answer probability when another word wt is predicted from a plurality of words wt−k, . . . , wt+k.

Meanwhile, the probability P $(w_j|d_i)$ shown in Equation (1) used in the present embodiment represents a correct answer probability that one word $w_j$ of n words is predicted from one text $d_i$ of m texts. Predicting one word $w_j$ from one text $d_i$ means that, specifically, when a certain text $d_i$ appears, a possibility of including the word $w_j$ in the text $d_i$ is predicted.

In Equation (1), an exponential function value is used, where e is the base and the inner product of the word vector w→ and the text vector d→ is the exponent. Then, a ratio of an exponential function value calculated from a combination of a text $d_i$ and a word $w_j$ to be predicted to the sum of n exponential function values calculated from each combination of the text $d_i$ and n words Wk (k=1, 2, . . . , n) is calculated as a correct answer probability that one word $w_j$ is expected from one text $d_i$.

Here, the inner product value of the word vector $w_j$→ and the text vector $d_i$→can be regarded as a scalar value when the word vector $w_j$→ is projected in a direction of the text vector $d_i$→, that is, a component value in the direction of the text vector $d_i$→included in the word vector $w_j$→, which can be considered to represent a degree at which the word $w_j$ contributes to the text $d_i$. Therefore, obtaining the ratio of the exponential function value calculated for one word $W_j$ to the sum of the exponential function values calculated for n words Wk (k=1, 2, . . . , n) using the exponential function value calculated using the inner product corresponds to obtaining the correct answer probability that one word $w_j$ of n words is predicted from one text $d_i$.

Note that since Equation (1) is symmetrical with respect to $d_i$ and $w_j$, a probability P $(d_i|w_j)$ that one text $d_i$ of m texts is predicted from one word $w_j$ of n words may be calculated. Predicting one text $d_i$ from one word $w_j$ means that, when a certain word $w_j$ appears, a possibility of including the word $w_j$ in the text $d_i$ is predicted. In this case, an inner product value of the text vector $d_i$→ and the word vector $w_j$→ may be regarded as a scalar value obtained when the text vector $d_i$→ is projected in a direction of the word vector $w_j$→, that is, a component value of the text vector $d_i$→ in the direction of the word vector $w_j$→. This can be considered as representing a degree to which the text $d_i$ contributes to the word $w_j$.

Note that here, a calculation example using the exponential function value using the inner product value of the word vector w→ and the text vector d→ as an exponent has been described. However, the exponential function value may not be used. Any calculation formula using the inner product value of the word vector w→ and the text vector d→ may be used. For example, the probability may be obtained from the ratio of the inner product values itself (Performing predetermined calculation for causing the inner product value to be a positive value at all times (for example, inner product value+1) is included.).

Next, the vector computation unit 122 computes the text vector $d_i$→ and the word vector $w_j$→ that maximize a value L of the sum of the probability P $(w_j|d_i)$ computed by Equation (1) for all the set S as shown in the following Equation (2). That is, the text vector computation unit **122*a* and the word vector computation unit 122*b*** compute the probability P $(W_j|\ d_i)$ computed by Equation (1) for all combinations of the m texts and the n words, and compute the text vector $d_i$→ and the word vector $w_j$→ that maximize a target variable L using the sum thereof as the target variable L.

[Equation 2]

$$L = \sum_{d \in D} \sum_{w \in W} \#(w, d) p(w \mid d) \tag{2}$$

Maximizing the total value L of the probability $P(w_j|\ d_i)$ computed for all the combinations of the m texts and the n words corresponds to maximizing the correct answer probability that a certain word $w_j$(j=1, 2, . . . , n) is predicted from a certain text $d_i$(i=1, 2, . . . , m). That is, the vector computation unit 122 can be considered to compute the text vector $d_i$→ and the word vector $w_j$→ that maximize the correct answer probability.

As described above, in the present embodiment, the vector computation unit 122 converts each of the m texts $d_i$ into a q-dimensional vector to compute the m texts vectors $d_i$→including the q axis components, and converts each of the n words into a q-dimensional vector to compute the n word vectors $w_j$→including the q axis components, which corresponds to computing the text vector $d_i$→ and the word vector $w_j$> that maximize the target variable L by making q axis directions variable.

The index value vector computation unit 123 computes each of the inner products of the m text vectors $d_i$→ and the n word vectors $w_j$→computed by the vector computation unit 122, thereby computing m×n relationship index values reflecting the relationship between the m texts $d_i$ and the n words $w_j$. In the present embodiment, as shown in the following Equation (3), the index value vector computation unit 123 obtains the product of a text matrix D having the respective q axis components ($d_{11}$ to $d_{mq}$) of the m text vectors $d_i$→ as respective elements and a word matrix W having the respective q axis components ($w_{11}$ to $W_{ng}$) of the n word vectors $w_j$→ as respective elements, thereby computing an index value matrix DW having m×n relationship index values as elements. Here, $W^+$ is the transposed matrix of the word matrix.

[Equation 3]

$$D=\begin{bmatrix} d_{11} & d_{12} & \cdots & d_{1q} \\ d_{21} & d_{22} & \cdots & d_{2q} \\ \vdots & \vdots & \ddots & \vdots \\ d_{m1} & d_{m2} & \cdots & d_{mq} \end{bmatrix} \quad W=\begin{bmatrix} w_{11} & w_{12} & \cdots & w_{1q} \\ w_{21} & w_{22} & \cdots & w_{2q} \\ \vdots & \vdots & \ddots & \vdots \\ w_{m1} & w_{m2} & \cdots & w_{mq} \end{bmatrix} \tag{3}$$

$$DW = D * W^t = \begin{bmatrix} dw_{11} & dw_{12} & \cdots & dw_{1n} \\ dw_{21} & dw_{22} & \cdots & dw_{2n} \\ \vdots & \vdots & \ddots & \vdots \\ dw_{m1} & dw_{m2} & \cdots & dw_{mn} \end{bmatrix}$$

Each element $dw_{ij}$ (i=1, 2, . . . , m, j=1, 2, . . . , n) of the index value matrix DW computed in this manner may indicate which word contributes to which text and to what extent. For example, an element $dw_{12}$ in the first row and the second column is a value indicating a degree at which the word $w_2$ contributes to a text $d_i$. In this way, each row of the index value matrix DW can be used to evaluate the similarity of a text, and each column can be used to evaluate the similarity of a word.

The index value vector computation unit 123 uses the index value matrix DW (m×n relationship index values) computed as in Equation (3) to specify a text index value group including n relationship index values $dw_{ij}$ (j=1, 2, . . . , n) for one text $d_i$ as an index value vector. Then, the specified index value vector of the text $d_i$ is output as a feature vector of the text $d_i$, that is, a feature vector of conversation data of a subject i.

Figure 3:
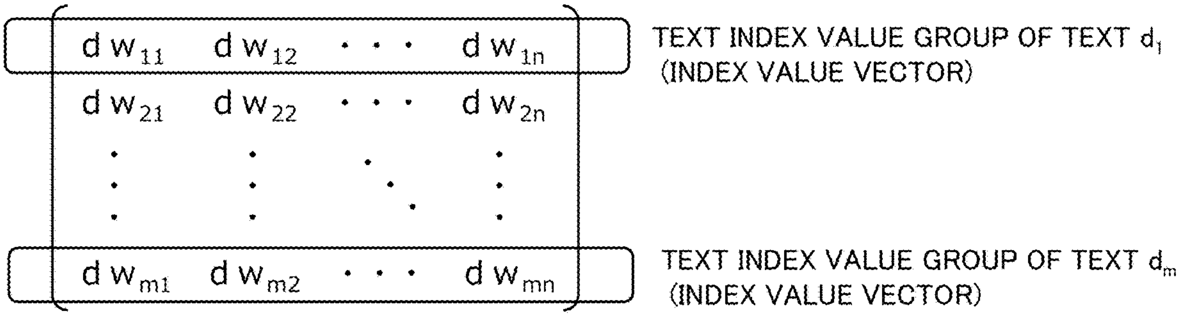
FIG. 3 is a diagram for describing a text index value group computed by an index value vector computation unit of this embodiment.

FIG. 3 is a diagram for describing a text index value group (index value vector). As illustrated in FIG. 3, for example, in the case of a first text $d_i$, n relationship index values $dw_{11}$ to $dw_{1n}$ included in a first row of the index value matrix DW correspond to a text index value group. Similarly, in the case of a second text $d_2$, n relationship index values $dw_{21}$ to $dw_{2n}$ included in a second row of the index value matrix DW correspond thereto. Then, this description is similarly applied up to a text index value group (n relationship index values $dw_{m1}$ to $dw_{mn}$) related to an mth text dm.

Note that, here, as illustrated in FIG. 3, even though an example of constructing a feature vector by a text index value group of each column in the index value matrix DW has been described, the invention is not limited thereto. For example, a text vector computed by the text vector computation unit 122*a* may be used as a feature vector.

A description will be given by returning to FIG. 1. The depressive symptom determination unit 13 determines a depressive symptom of a subject by inputting a feature vector computed by the feature vector computation unit 12 to a machine-trained determination model stored in the determination model storage unit 14. This determination model is a model that classifies a determination target subject using two values, that is, whether the HAMD score is 8 points or more or less than 8 points, and is a model that receives input of a feature vector and outputs the HAMD score or an evaluation value indicating whether the HAMD score is 8 points or more.

In this in this embodiment, the Hamilton depression evaluation scale (HAMD-17) is used as an example of a depression evaluation scale. As described above, in general, in HAMD-17, a person having a HAMD score of 7 points or less is diagnosed with a healthy person, and a person having a HAMD score of 8 points or more is diagnosed with a depressed patient (including mild, moderate, severe, and extremely severe). In this embodiment, according thereto, whether the HAMD score is 8 points or more is determined by the determination model.

For example, this determination model can be generated by ensemble learning such as XGBoost, which is a method of gradient boosting. Note that the form of the determination model is not limited thereto. For example, other tree models such as a decision tree, a regression tree, and a random forest may be used. Alternatively, a neural network model, a clustering model, etc. may be used.

The determination model of this embodiment is machine-trained using, as training data, feature vectors of a plurality of subjects satisfying a predetermined extraction condition and an exclusion condition related to a depressive symptom. The extraction condition is a condition for extracting a subject diagnosed with depression by a doctor and a subject not diagnosed with either manic-depressive or depression. The exclusion condition is a condition for excluding a subject whose predetermined manic-depressive evaluation scale score is greater than or equal to a manic-depressive threshold.

In this embodiment, the Young Mania Rating Scale (YMRS) is used as an example of a manic-depressive evaluation scale. The YMRS is an evaluation scale based on a clinical interview and having 11 items including elation and increased activity. In this embodiment, the manic-depressive threshold of the exclusion condition is set to 8 points, and training data is constructed by excluding a subject whose total value of a score for each item (hereinafter referred to as YMRS score) is 8 points or more.

In this embodiment, the determination model is machine-trained using a feature vector computed from conversation data of each subject, with a subject whose HAMD score is 8 or more as a positive example and a subject whose HAMD score is less than 8 as a negative example among subjects satisfying the above-mentioned extraction condition and exclusion condition.

Figure 4:
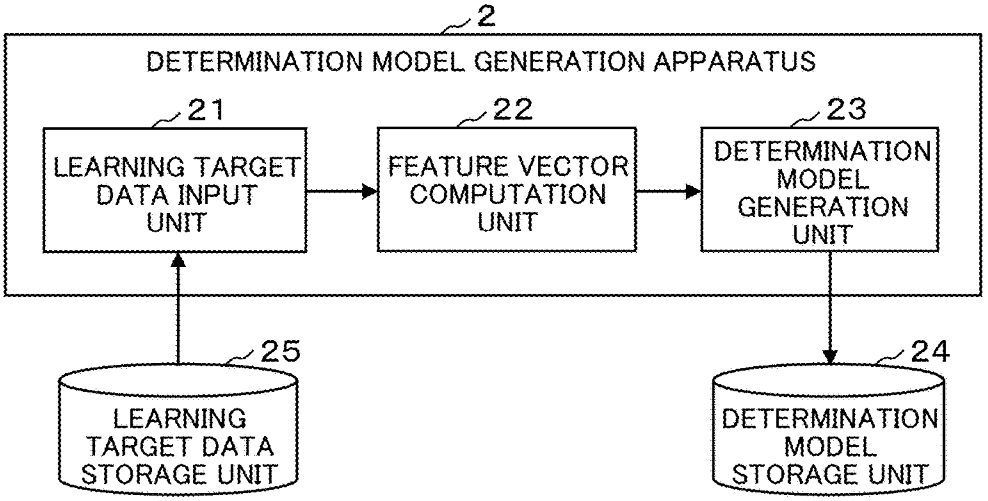
FIG. 4 is a block diagram illustrating a functional configuration example of a determination model generation apparatus according to this embodiment.

FIG. 4 is a block diagram illustrating a functional configuration example of a determination model generation apparatus 2 according to this embodiment. As illustrated in FIG. 4, the determination model generation apparatus 2 of this embodiment includes, as a functional configuration, a learning target data input unit 21, a feature vector computation unit 22, and a determination model generation unit 23. In addition, a determination model storage unit 24 and a learning target data storage unit 25 are connected as storage media to the determination model generation apparatus 2 of this embodiment.

The functional blocks 21 to 23 can be configured by any of hardware, a DSP, and software. For example, the functional blocks 21 to 23 are realized by an operation of a program stored in a storage medium such as a RAM, a ROM, a hard disk, or a semiconductor memory under the control of a microcomputer including a CPU, a RAM, a ROM, etc. Instead of or in addition to the CPU, a GPU, an FPGA, an ASIC, a DSP, etc. may be used.

The learning target data input unit 21 inputs, as learning target data, a plurality of pieces of conversation data each representing content of conversations that a plurality of subjects (hereinafter, referred to as condition-applicable subjects) satisfying a predetermined extraction condition and exclusion condition with respect to a depressive symptom conducts. In this embodiment, as an example of conversation data, character data of a text representing content of a conversation is input as learning target data.

Processing content for the learning target data input unit 21 to input conversation data of the plurality of subjects as text is similar to that of the determination target data input unit 11 illustrated in FIG. 1. A difference from the determination target data input unit 11 is that the learning target data input unit 21 inputs conversation data related to a condition-applicable subject as learning target data.

For example, the learning target data storage unit 25 stores conversation data of a condition-applicable subject (which may be voice data of conversation or text data converted from voice data into text). The learning target data input unit 21 inputs learning target data by reading the conversation data of the condition-applicable subject from the learning target data storage unit 25. Here, when voice data is stored in the learning target data storage unit 25, the learning target data input unit 21 replaces the voice data of the conversation read from the learning target data storage unit 25 with character data, and uses this data as learning target data.

In this example, the learning target data stored in the learning target data storage unit 25 is generated by a learning target data generation apparatus 3 having a function of a learning target data generation unit 31, for example, as illustrated in FIG. 5. In an example illustrated in FIG. 5, a conversation data storage unit 32 stores, in addition to the conversation data of the condition-applicable subject, conversation data (which may be voice data of the conversation or text data converted from voice data into text) of a subject not satisfying the predetermined extraction condition and exclusion condition (hereinafter referred to as a condition-non-applicable subject). In addition, the conversation data storage unit 32 stores information necessary for determining whether or not the predetermined extraction condition and exclusion condition are satisfied in association with the conversation data. The information necessary for determining whether or not the conditions are satisfied is information indicating whether or not a subject is diagnosed with depression or manic-depressive by the doctor, and a HAMD score and a YMRS score of the subject. The HAMD score and the YMRS score are obtained by performing evaluation when the conversation data is recorded.

The learning target data generation unit 31 generates learning target data by extracting conversation data of a condition-applicable subject from the conversation data storage unit 32 based on information stored in the conversation data storage unit 32 in association with the conversation data, and stores the generated learning target data in the learning target data storage unit 25. Here, the learning target data generation unit 31 labels conversation data of a subject whose HAMD score is 8 or more with a positive example while labeling conversation data of a subject whose HAMD score is less than 8 with a negative example among conversation data of extracted condition-applicable subjects.

Note that, when the conversation data stored in the conversation data storage unit 32 is voice data, the learning target data generation unit 31 may store voice data read from the conversation data storage unit 32 as learning target data in the learning target data storage unit 25, or may replace the voice data read from the conversation data storage unit 32 with character data and store the character data as learning target data in the learning target data storage unit 25.

Note that a method of generating the learning target data is not limited thereto. For example, a conversation may be recorded only for a subject satisfying the predetermined extraction condition and exclusion condition, and conversation data obtained thereby may be stored in the learning target data storage unit 25 as learning target data.

The function of the learning target data generation unit 31 may be comprised by the learning target data input unit 21. In this case, the learning target data input unit 21 has both functions of generating and inputting learning target data. That is, the learning target data input unit 21 generates learning target data by extracting (inputting) conversation data of a condition-applicable subject from conversation data of a plurality of subjects stored in the conversation data storage unit 32.

Returning to FIG. 4, the feature vector computation unit 22 obtains a feature vector by computing feature quantities of a plurality of pieces of conversation data input by the learning target data input unit 21 and converting the feature quantities into a vector. When text (character data) representing content of a conversation is used as an example of conversation data, the feature vector computation unit 22 computes a feature quantity of the text and converts the feature quantity into a vector. Processing content for conversion into a vector is similar to that of the feature vector computation unit 12 illustrated in FIG. 1. The feature vector computed by the feature vector computation unit 22 is used as training data when a determination model is machine-trained.

Note that a method of generating training data in the claims is realized by processing of the learning target data generation unit 31, the learning target data input unit 21, and the feature vector computation unit 22. That is, training data generation unit is composed of the learning target data generation unit 31, the learning target data input unit 21, and the feature vector computation unit 22.

The determination model generation unit 23 performs machine learning using a feature vector computed by the feature vector computation unit 22 as training data, thereby generating a determination model for determining a depressive symptom of the subject based on the feature vector. As described above, in this embodiment, machine learning is performed using, as training data, a feature vector computed from learning target data generated based on conversation data of a condition-applicable subject.

Here, the determination model generation unit 23 performs machine learning using, as a positive example, a feature vector generated from conversation data labeled with a positive example (conversation data of a subject whose HAMD score is 8 or more) and using, as a negative example, a feature vector generated from conversation data labeled with a negative example (conversation data of a subject whose HAMD score is less than 8) among pieces of conversation data of condition-applicable subjects.

Then, the determination model generation unit 23 causes the determination model storage unit 24 to store a determination model generated by machine learning. The determination model stored in the determination model storage unit 24 is stored in the determination model storage unit 14 illustrated in FIG. 1. Note that the determination model storage unit 24 illustrated in FIG. 4 may be the same as the determination model storage unit 14 illustrated in FIG. 1.

Even though an example in which the depressive symptom determination apparatus 1 and the determination model generation apparatus 2 are separately configured has been described above, a part may be shared. For example, the feature vector computation units 12 and 22 may be shared.

As described above, in this embodiment, while training data is generated from conversation data of a subject diagnosed with depression by a doctor and a subject not diagnosed with either manic-depressive or depression, training data is configured using a subject whose HAMD score is 8 points or more as a positive example and using a subject whose HAMD score is less than 8 points as a negative example, and the determination model is machine-trained using the training data configured in this way.

In this way, a depressive symptom is determined based on a feature of a conversation conducted by a determination target subject using a determination model machine-trained using a feature vector computed based on a feature quantity of a conversation, and thus it is possible to determine a depressive symptom when the subject is conducted the conversation. In addition, while an extraction condition is set based on a diagnosis result of a doctor, training data is labeled with a positive example/negative example based on a HAMD score. Therefore, a depressive symptom can be determined according to a state of a subject when a conversation is conducted even for a subject temporarily in a state different from a diagnosis result for a depressive symptom by a doctor. In this way, a depressive symptom of the subject at the time can be determined by a determination model regardless of the diagnosis result for the depressive symptom by the doctor.

Further, in this embodiment, training data is configured by excluding a subject whose YMRS score is 8 points or more, and the determination model is machine-trained using the training data configured in this way. The determination model machine-trained using such training data can be regarded as a determination model machine-trained without being affected by conversation data of a subject whose HAMD score is less than 8 when manic-depressive disorder is temporarily in a manic state.

In this embodiment, the determination model configured in this way is used to determine a depressive symptom of the determination target subject. For this reason, the depressive symptom of the determination target subject can be more accurately determined such that a feature of a conversation when a manic-depressive patient is temporarily in a manic state can be distinguished.

In general, it is considered that there are two types of anxiety related to a depressive symptom. One type is trait anxiety and the other type is state anxiety. Trait anxiety refers to nature coming from personality of a person and having a tendency to become anxious and does not change much depending on the situation. On the other hand, state anxiety refers to a temporary anxiety reaction to a specific time, scene, event, or object. The determination model of this embodiment is particularly effective in determining presence/absence of depressive symptoms caused by state anxiety.

Note that, in the above embodiment, an example in which a subject whose predetermined manic-depressive evaluation scale score is greater than or equal to the manic-depressive threshold are used as the exclusion condition has been described. In contrast to this, a subject whose depression evaluation scale score is greater than or equal to a second depression threshold greater than the depression threshold may be further added to the exclusion condition. For example, a condition for excluding a subject whose HAMD score is 19 points or more (patient with severely or extremely severe depressed) may be further added.

The inventors confirmed that a feature vector computed from conversation data of a subject whose HAMD score is 19 points or more is significantly different from a feature vector computed from conversation data of a subject whose HAMD score is 18 points or less. Therefore, as a result of generating training data by excluding conversation data of the subject whose HAMD score is 19 points or more and performing machine learning of a determination model based thereon, it was confirmed that accuracy of determining a depressive symptom for the subject whose HAMD score is 18 points or less was improved.

FIG. 6 is a diagram illustrating a result of determining a depressive symptom using, as a determination target, conversation data of a depressed patient diagnosed with depression by a doctor and conversation data of a healthy person not diagnosed with depression using the depressive symptom determination apparatus 1 of this embodiment. Here, this figure illustrates a result of performing determination by a determination model machine-trained based on training data generated by adding a condition that a subject whose HAMD score is 19 points or more is excluded (this description is similarly applied to FIG. 7 and FIG. 8 illustrated below). As illustrated in FIG. 6, the numbers of false negatives (FN) and false positives (FP) are significantly small when compared to the numbers of true negatives (TN) and true positives (TP), with accuracy rate of the depressive symptom based on the HAMD score was 83.10%, a recall rate thereof was 92.16%, and a precision rate thereof was 85.45%.

FIG. 7 is a diagram illustrating a result of determining a depressive symptom using conversation data of a depressed patient whose HAMD score is 19 points or more and conversation data of a healthy person as determination targets by using a determination model generated by adding a condition for excluding a subject whose HAMD score is 19 points or more similarly to the above description. As illustrated in FIG. 7, the numbers of false negatives (FN) and false positives (FP) are significantly small when compared to the numbers of true negatives (TN) and true positives (TP). An accuracy rate and a recall rate of the depressive symptom based on the HAMD score were 80.22%, and a precision rate thereof was 100%. As described above, even though the training data was generated by excluding the subject whose HAMD score was 19 points or more, it is possible to determine with high accuracy a depressive symptom of a depressed patient whose HAMD score is 19 points or more.

Note that, in the embodiment, an example in which character data of a plurality of speech parts included in a single conversation of one subject is collectively defined as one text has been described. However, character data of a plurality of speech parts may be treated as a plurality of texts. In this case, the determination model is generated as a model that determines a depressive symptom by inputting a plurality of feature vectors for a single subject.

In addition, in the embodiment, an example in which a text representing content of a conversation is used as an example of conversation data, and the text index value group illustrated in FIG. 3 is used as a feature vector has been described. However, the feature vector is not limited thereto. In other words, it is sufficient that the feature vector is a vector having, as elements, a plurality of feature quantities representing features of content or voice of a conversation conducted by a subject. For example, the feature vector may be generated by extracting a plurality of types of acoustic features (a prosodic feature such as pause duration, pitch, or an energy measurement value, a voice phonetic feature such as a fundamental frequency, a formant frequency, or an average Hibert envelope, various cepstrum coefficients, etc.) from conversation voice.

Further, in the embodiment, as described above, an example in which 8 points of the HAMD score (a minimum value determined as mild) is used as the depression threshold for distinguishing between a positive example and a negative example has been described. However, the invention is not limited thereto. For example, 14 points of the HAMD score (a minimum value determined as moderate) may be used. Further, in the embodiment, an example in which 8 points of the YMRS score is used as the manic-depressive threshold of the exclusion condition has been described. However, the invention is not limited thereto.

Further, in the embodiment, a description has been given of an example in which the Hamilton Depression Scale (HAMD-17) is used as an example of the depression evaluation scale, and the Young Mania Rating Scale (YMRS) is used as an example of the manic-depressive evaluation scale. However, the invention is not limited thereto. For example, the Hamilton Anxiety Scale (HAMA), the CPRG Depression Rating Scale (CPRG-D), the inventory of Depressive Symptomatology (IDS), etc. may be used instead of HAMD-17. Further, the Bipolar Depression Rating Scale (BDRS), the CPRG Mania Rating Scale (CPRG-M), the Manic Diagnostic and Severity Scale (MADS), etc. may be used instead of YMRS.

Further, in the embodiment, a description has been given of an example in which the depressive symptom determination apparatus 1 includes the feature vector computation unit 12. However, the invention is not limited thereto. For example, the feature vector computation unit 12 may be provided in an apparatus other than the depressive symptom determination apparatus 1, and a feature vector generated by the other apparatus may be input to the depressive symptom determination apparatus 1.

Similarly, the feature vector computation unit 22 may be provided in an apparatus other than the determination model generation apparatus 2, and a feature vector generated by the other apparatus may be input to the determination model generation apparatus 2. For example, as illustrated in FIG. 8, it is possible to employ a configuration including a training data generation apparatus 4 illustrated in FIG. 8 (*a*) and a determination model generation apparatus 2' illustrated in FIG. 8 (*b*).

As illustrated in FIG. 8 (*a*), the training data generation apparatus 4 includes, as a functional configuration, a learning target data generation unit 31 and the feature vector computation unit 22. Functions thereof are the same as those illustrated in FIG. 4 and FIG. 5. The feature vector computation unit 22 stores a computed feature vector as training data in the training data storage unit 41. In this case, a training data generation unit is composed of the learning target data generation unit 31 and the feature vector computation unit 22.

As illustrated in FIG. 8(*b*), the determination model generation apparatus 2' includes, as a functional configuration, a training data input unit 42 and a determination model generation unit 23. A function of the determination model generation unit 23 is the same as that illustrated in FIG. 4. The training data input unit 42 inputs training data (feature vector) stored in the training data storage unit 41. The determination model generation unit 23 generates a determination model by performing machine learning using the training data input by the training data input unit 42.

In addition, all the embodiments are merely examples of embodiment in carrying out the invention, and the technical scope of the invention should not be construed in a limited manner by the embodiments. That is, the invention can be implemented in various forms without departing from a gist or a main feature thereof.

REFERENCE SIGNS LIST

1: depressive symptom determination apparatus
2, 2': determination model generation apparatus
3: learning target data generation apparatus
4: training data generation apparatus
11: determination target data input unit
12: feature vector computation unit
13: depressive symptom determination unit

14: determination model storage unit
21: learning target data input unit
22: feature vector computation unit
23: determination model generation unit
24: determination model storage unit
25: learning target data storage unit
31: learning target data generation unit
32: conversation data storage unit
41: training data storage unit
42: training data input unit
121: word extraction unit
122: vector computation unit
**122*a***: text vector computation unit
**122*b***: word vector computation unit
123: index value vector computation unit

The invention claimed is:

1. A depressive symptom determination apparatus comprising a processor and a memory and further characterized by comprising:

a depressive symptom determination unit configured to determine a depressive symptom of a subject by inputting a feature vector computed based on a feature quantity of a conversation conducted by the subject as a determination target to a machine-trained determination model, wherein the determination model is machine-trained using, as training data, the feature vector for a plurality of subjects satisfying a predetermined extraction condition and exclusion condition related to a depressive symptom, by using, as a positive example, the feature vector generated from conversation data labeled with a positive example and using, as a negative example, the feature vector generated from conversation data labeled with a negative example, and the training data are generated by the following processing processing, based on the information indicating whether or not the subject is diagnosed with depression or manic-depressive disorder by a doctor, and a manic-depressive disorder evaluation scale score of the subject, both of which are stored with conversation data of the subject in a storage unit, of extracting, from the storage unit, the conversation data satisfying both of the extraction condition for extracting conversation data of a subject diagnosed with depression, and conversation data of a subject not diagnosed with either manic-depressive disorder or depression and the exclusion condition for excluding conversation data of a subject whose manic-depressive disorder evaluation scale score is greater than or equal to a manic-depressive disorder threshold;

processing, based on a depression evaluation scale score of the subject stored with conversation data of the subject in the storage unit, of labeling, with a positive example, conversation data of a subject whose depression evaluation scale score is greater than or equal to a depression threshold and labeling with a negative example conversation data of a subject whose depression evaluation scale score is less than the depression threshold among the conversation data that has been extracted from the storage unit and processing of generating the training data by computing the feature vector from the conversation data, wherein the conversation data comprises, for each of the plurality of subjects, a text converted from voice data of a conversation of the subject, and computing the feature vector comprises:

extracting a plurality of words from the texts of the plurality of subjects;

computing a text vector for each of the texts and a word vector for each of the words such that the text vectors and the word vectors maximize a total value of a probability, computed using an inner product of the respective text vector and the respective word vector, that each of the words is predicted from each of the texts;

computing an index value matrix whose elements are relationship index values, each computed as an inner product of one of the text vectors and one of the word vectors; and outputting, as the feature vector of the conversation data of one subject, the relationship index values of the row of the index value matrix corresponding to the text of the one subject.

2. The depressive symptom determination apparatus according to claim 1, characterized in that the exclusion condition is a condition for further excluding conversation data of a subject whose depression evaluation scale score is greater than or equal to a second depression threshold greater than the depression threshold.

3. A determination model generation apparatus comprising a processor and a memory and further characterized by comprising:

a determination model generation unit configured to perform machine learning using, as training data, a feature vector computed based on a feature quantity of a conversation conducted by a plurality of subjects satisfying a predetermined extraction condition and exclusion condition with regard to a depressive symptom, by using, as a positive example, the feature vector generated from conversation data labeled with a positive example, and using, as a negative example the feature vector generated from conversation data labeled with a negative example, thereby generating a determination model for determining a depressive symptom of the subject based on the feature vector, wherein the training data are generated by the following processing:

processing, based on the information indicating whether or not the subject is diagnosed with depression or manic-depressive disorder by a doctor, and a manic-depressive disorder evaluation scale score of the subject, both of which are stored with conversation data of the subject in a storage unit, of extracting, from the storage unit, the conversation data satisfying both of the extraction condition for extracting conversation data of a subject diagnosed with depression, and conversation data of a subject not diagnosed with either manic-depressive disorder or depression, and the exclusion condition excluding conversation data of a subject whose manic-depressive disorder evaluation scale score is greater than or equal to a manic-depressive disorder threshold, processing, based on a depression evaluation scale score of the subject stored with conversation data of the subject in the storage unit, of labeling, with a positive example, conversation data of a subject whose depression evaluation scale score is greater than or equal to a depression threshold and labeling, with a negative example, conversation data of a subject whose depression evaluation scale score is less than the depression threshold among the conversation data that has been extracted from the storage unit and processing of generating the training data by computing the feature vector from the conversation data, wherein the conversation data comprises, for each of the plurality of subjects, a text converted from voice data of a conversation of the subject, and computing the feature vector comprises:

extracting a plurality of words from the texts of the plurality of subjects;

computing a text vector for each of the texts and a word vector for each of the words such that the text vectors and the word vectors maximize a total value of a probability, computed using an inner product of the respective text vector and the respective word vector, that each of the words is predicted from each of the texts;

computing an index value matrix whose elements are relationship index values, each computed as an inner product of one of the text vectors and one of the word vectors; and outputting, as the feature vector of the conversation data of one subject, the relationship index values of the row of the index value matrix corresponding to the text of the one subject.

4. The determination model generation apparatus according to claim 3, characterized in that the exclusion condition is a condition for further excluding conversation data of a subject whose depression evaluation scale score is greater than or equal to a second depression threshold greater than the depression threshold.

5. A method of generating training data used when machine-training a determination model configured to determine a depressive symptom of a subject, the method characterized by comprising steps of:

generating, by a training target data generation unit of a computer, based on the information indicating whether or not the subject is diagnosed with depression or manic-depressive disorder by a doctor, a depression evaluation scale score and a manic-depressive disorder evaluation scale score of the subject, all of which are stored with conversation data of the subject in a storage unit, training target data by extracting, from the storage unit conversation data satisfying both of an extraction condition for extracting conversation data of a subject diagnosed with depression, and conversation data of a subject not diagnosed with either manic-depressive disorder or depression, and an exclusion condition for excluding conversation data of a subject whose manic-depressive disorder evaluation scale score is greater than or equal to a manic-depressive disorder threshold, and by labelling, with a positive example, conversation data of a subject whose depression evaluation scale score is greater than or equal to a depression threshold and labelling, with a negative example, conversation data of a subject whose depression evaluation scale score is less than the depression threshold among the conversation data that has been extracted; and computing, by a feature vector computation unit of the computer, a feature vector from the conversation data determined by the training target data generation unit to be the training target data, thereby generating the training data, wherein the conversation data comprises, for each of the plurality of subjects, a text converted from voice data of a conversation of the subject, and computing the feature vector comprises:

extracting a plurality of words from the texts of the plurality of subjects;

computing a text vector for each of the texts and a word vector for each of the words such that the text vectors and the word vectors maximize a total value of a probability, computed using an inner product of the respective text vector and the respective word vector, that each of the words is predicted from each of the texts;

computing an index value matrix whose elements are relationship index values, each computed as an inner product of one of the text vectors and one of the word vectors; and outputting, as the feature vector of the conversation data of one subject, the relationship index values of the row of the index value matrix corresponding to the text of the one subject.

6. The method of generating training data according to claim 5, characterized in that the exclusion condition is a condition for further excluding conversation data of a subject whose depression evaluation scale score is greater than or equal to a second depression threshold greater than the depression threshold.

* * * * *